United States Patent
De Munck et al.

(10) Patent No.: US 8,729,289 B2
(45) Date of Patent: May 20, 2014

(54) ESTER PRODUCTION

(75) Inventors: Nicolaas Anthony De Munck, Barendrecht (NL); Allen David Godwin, Seabrook, TX (US); Thomas Marshall Larson, Bellaire, TX (US); Paul H. Daniels, League City, TX (US); Didier Naert, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 1252 days.

(21) Appl. No.: 12/526,735

(22) PCT Filed: Mar. 7, 2008

(86) PCT No.: PCT/EP2008/001836
§ 371 (c)(1),
(2), (4) Date: Dec. 14, 2009

(87) PCT Pub. No.: WO2008/110304
PCT Pub. Date: Sep. 18, 2008

(65) Prior Publication Data
US 2010/0108940 A1    May 6, 2010

Related U.S. Application Data

(60) Provisional application No. 60/906,732, filed on Mar. 13, 2007, provisional application No. 60/933,821, filed on Jun. 8, 2007.

(51) Int. Cl.
*C07C 69/74*    (2006.01)

(52) U.S. Cl.
USPC .......................................................... 560/1

(58) Field of Classification Search
USPC .......... 560/1, 98, 112, 126, 182, 64; 524/297, 524/287, 284, 556, 296, 315, 314, 298; 526/344; 427/196, 208.8; 106/14.35, 106/14.41, 14.13; 585/16; 562/599; 508/463, 482, 496; 252/182.12
See application file for complete search history.

(56) References Cited

U.S. PATENT DOCUMENTS

| | | |
|---|---|---|
| 5,236,987 A | 8/1993 | Arendt |
| 5,324,853 A | 6/1994 | Jones et al. |
| 5,880,310 A | 3/1999 | Ageishi et al. |
| 6,310,235 B1 | 10/2001 | Gick |
| 6,355,817 B1 | 3/2002 | Woods et al. |
| 2004/0015007 A1 | 1/2004 | Grass et al. |
| 2004/0138358 A1 | 7/2004 | Koch et al. |
| 2004/0260113 A1* | 12/2004 | Bueschken et al. ........... 560/127 |
| 2007/0010599 A1 | 1/2007 | Grass et al. |
| 2010/0130767 A1 | 5/2010 | De Munck et al. |
| 2010/0137631 A1 | 6/2010 | De Munck et al. |

FOREIGN PATENT DOCUMENTS

| | | |
|---|---|---|
| WO | WO 2005/021482 | 3/2005 |
| WO | WO 2006/077131 | 7/2006 |
| WO | WO 2006/125670 | 11/2006 |
| WO | WO 2006/125670 A1 * | 11/2006 |

* cited by examiner

*Primary Examiner* — Wu-Cheng Winston Shen
*Assistant Examiner* — Blaine G Doletski
(74) *Attorney, Agent, or Firm* — Leandro Arechederra, III

(57) ABSTRACT

A method for performing a flying grade switch in an ester production process, which preferably is operated in semi-continuous mode, maximizes plant equipment productivity while minimizing product cross-contamination. Mixed ester products of the process containing a $C_9$-$C_{11}$ alkyl or isodecyl benzoate together with a higher molecular weight di-alkyl phthalate or cyclohexanoate, bring performance advantages such as improved permanence in plasticized PVC articles or improved processability in manufacturing these articles.

5 Claims, No Drawings

US 8,729,289 B2

ESTER PRODUCTION

CROSS REFERENCE TO RELATED APPLICATIONS

This application is a 371 National Stage Application of International Application No. PCT/EP2008/001836, filed Mar. 7, 2008, which claims the benefit of Provisional Application Nos. 60/906,732, filed Mar. 13, 2007, and 60/933,821, filed on Jun. 8, 2007, the disclosures of which are herein incorporated by reference in their entireties.

FIELD OF THE INVENTION

The invention relates to the production of different esters in the same process, to the product compositions derived therefrom that contain benzoates derived from $C_{10}$ alcohols, to certain uses of such product compositions, and to a system for carrying out said production.

BACKGROUND OF THE INVENTION

Esters are produced by the reaction of an alcohol with a carboxylic acid or a carboxylic acid anhydride. In many instances, one or more of the starting materials may be mixtures. The carboxylic acid may be a mono or a polycarboxylic acid or the anhydride thereof. Plasticiser esters are generally produced from polycarboxylic acids or the anhydrides thereof and in particular from phthalic anhydride, cyclohexane dicarboxylic acid or its anhydride, terephthalic acid, adipic acid or trimellitic acid or anhydride. Esters of benzoic acid or the anhydride thereof, such as isononyl benzoate or isodecyl benzoate, are examples of plasticiser mono-esters. Esters may be produced from any alcohol, but plasticiser esters are generally produced from C4 to C13 alcohols and in particular C6 to C13 alcohols more typically C8 to C10 alcohols.

The production of esters and in particular plasticiser esters are described in patents too numerous to list. Examples include U.S. Pat. Nos. 5,324,853; 5,880,310; 6,310,235, and 6,355,817, and PCT publications WO 2006/077131 and WO 2006/125670.

US 2004/0015007 discloses isomeric nonyl benzoates and mixtures thereof with alkyl phthalate, alkyl adipate or alkyl cyclohexane dicarboxylate. The mixtures disclosed contain at least 1% by weight of isomeric isononyl benzoates and US 2004/0015007 is silent about the possible presence of benzoates derived from $C_{10}$ alcohols.

Isodecyl benzoates are disclosed in U.S. Pat. No. 5,236,987 and US 2007/0010599. These publications are silent about possible mixtures thereof with other esters, such as alkyl phthalates, adipates or cyclohexane dicarboxylates.

A specific isodecyl benzoate, including from 50 to 99% of 2-propylheptyl benzoate and from 1 to 50% of at least one selected from a group of other specific isodecyl benzoate isomers is disclosed in US 2004/0138358. Further disclosed are compositions including from 5 to 90% by weight of this specific isodecyl benzoate and from 10 to 95% by weight of another ester selected from a di-$C_4$-$C_{13}$ alkyl phthalate, such as di-isononyl phthalate, a di-$C_4$-$C_{13}$ alkyl adipate, such as di-isononyl adipate and di-$C_4$-$C_{13}$ alkyl cyclohexane dicarboxylate, such as di-isononyl cyclohexane dicarboxylate.

Plasticiser esters may be produced in batch mode. Due to their high production volumes, they are preferably produced in continuous mode or in semi-continuous mode. The esterification process is particularly suited for production in semi-continuous mode. In semi-continuous esterification operations, the esterification reactors are typically operated in batch mode, the crude ester products from the different reactor batches then being collected and processed in continuous mode through a finishing section for product clean-up and purification. Suitable esterification processes are also disclosed in co-pending U.S. patent applications 60/906797 or 60/906732. The finishing section typically comprises catalyst removal, neutralisation of leftover traces of acid, separation of catalyst residues and/or salts from the neutralisation, separation and recovery of excess alcohol. A detailed description of an esterification finishing section and how it may be operated is disclosed in WO2005/021482 or WO2006/125670.

Operating the finishing section in continuous mode creates a problem when more than one ester product is produced in the same production facility, and when the esterification process has to switch from one product to another on a regular basis. A conventional method is to shut down and empty the finishing section of the process, and clean the equipment by e.g. a water wash before the next reaction product is fed to the finishing section. This introduces a significant amount of down time, and possibly generates substantial volumes of waste water that needs to be disposed of. An alternative is a dry changeover, thus eliminating the use of water, but which because of grade cross-contamination typically produces a certain volume of mixed grade product material, which is generally not compliant with any of the individual product grade specifications and therefore may need to be downgraded to a lower sensitivity end-use or be reworked.

The amount of such cross-contaminated or mixed grade product material may be significant, because the liquid hold-up in the equipment of the continuous finishing section may be important. Contributing to this liquid hold-up may be the liquid contained in any of the following equipment, when present:

the feed vessel to the finishing section;
the neutralisation vessel, wherein acids remaining from the esterification reaction are neutralised with a base, and wherein the catalyst (e.g., titanate catalyst), is removed such as by hydrolysing;
the water separator vessel conventionally placed after the primary filtration step, if the wet titanium process is used;
the water flash vessel, if the dry titanium process is used;
the filter aid mixing vessel, in the case where a primary filtration step using filter aid is included in the process;
the precoat vessel to the primary filtration, where precoat material, typically an inert material of a suitable granularity, may be mixed into product liquid before circulating this over a fresh primary filter to deposit the layer of precoat filter material on the filter before commisioning;
the primary filters themselves, when present, including the liquid contained in the filter cake;
the stripper, where excess alcohol may be stripped from the crude ester, typically after the primary filtration step, by using steam or nitrogen;
the product drying tower, when used, where steam stripped ester may be further dried in countercurrent with nitrogen;
the filter aid mixing vessel, precoat vessel and the filters comprised in a secondary filtration step, when used.

There remains therefore a need for a method for switching production from one product grade to a second product grade in an esterification process having a continuous finishing section, maximising equipment productivity while minimising product cross-contamination. The present inventors have found that such productivity benefits may be achieved, while keeping product contamination to an acceptable level, by applying a so-called "flying grade switch procedure". More-over, in embodiments, co-products from an esterification process employing such flying grade switch procedure on particular product grade sequences bring performance benefits.

SUMMARY OF THE INVENTION

The invention is directed to an esterification process wherein production is switched from a first ester product to a second, different, ester product, the product compositions produced thereby, and to a system for producing a mixed-ester product. The product compositions are especially useful as plasticizers for PVC, but may also be used in other applications such as polyurethane foams, printing inks, coil coating applications, blanket washes for litho presses, or as solvents in carbonless copy paper or agricultural chemical formulations.

In an embodiment, the process of the invention is particularly advantageous when both the acid and alcohol feed are switched, so that both the carboxylate and alkoxy moieties of the second ester product are different from the corresponding moieties of the first ester product.

In another embodiment, the invention provides for a method for switching production from a first ester product to a second and different ester product, in an esterification process that comprises a feed vessel for feeding a continuous finishing section which comprises at least one filtration step using solids addition for precoating a precoat filter, preferably by adding from a filter precoat vessel a precoat containing liquid to the ester before filtration, comprising the steps of, before introducing the second ester product into the feed vessel of the continuous finishing section,
a) reducing the level of the feed vessel, and preferably reducing the levels of all other mixing and intermediate vessels and towers (e.g., all vessel levels are gradually reduced to the minimum level required to keep the esterification unit pumps and mixers running);
b) optionally switching the precoat filter in service to a filter with a fresh precoat layer;
c) reducing the inventory or level of the precoat containing liquid in the filter precoat vessel,
introducing the second ester product into the feed vessel of the continuous finishing section, and after feeding from the feed vessel a preselected portion, preferably at least 80%, more preferably at least at 90% of the volume of the second ester, required for flushing out the first ester from the continuous finishing section,
d) redirecting the product rundown of the finishing section from the vessel receiving the first product ester to a different vessel for receiving the second product ester,
e) optionally re-establishing increased liquid levels in the filter precoat vessel, in the feed vessel to the continuous finishing section, and preferably in all other mixing and intermediate vessels and towers.

The invention further provides for an esterification process for producing a first ester product and subsequently producing a second ester product, comprising the method for switching production from the first ester product to the second ester product according to the present invention.

The esterification reactor or section may be operated in continuous mode or in batch mode. We prefer to operate the reactor section in batch mode, because this reduces the risk and amount of cross-contamination between different products produced on the same reaction section. A combination of batch reactors with a continuous finishing section is herein referred to as a semi-continuous esterification process.

In another embodiment, the method further comprises switching production from the second ester product to a second campaign of the first ester product, using steps a), b), c), d), and e), above, of the method of the invention, whereby the redirecting in step d) is performed after feeding at least 100% of the volume of the first ester, required for flushing out the second ester from the continuous finishing section. This method avoids the risk for cross-contamination of the second ester product with a third product ester that may be produced on the same process equipment, but for which the allowable cross-contamination levels may be significantly lower than between the first and the second ester product.

This "flying grade switch procedure" described by the embodiments above provides the benefit of minimizing production loss, because equipment downtime is avoided.

It is an object of the invention to provide a method for attenuation of the amount of different esters in a product composition comprising a mixture of two or more different esters. The method also allows the user to limit product cross-contamination between a first ester product and a second and different ester product.

The esterification process of the invention may be operated in semi-continuous mode, wherein one or more esterification reactors are fed from at least a first reactor feed vessel comprising a first alcohol and at least a second reactor feed vessel comprising a first acid or anhydride, and wherein the crude ester product from said one or more esterification reactors is collected in batches and processed continuously through a finishing section for at least one of catalyst removal, neutralisation of leftover traces of acid, separation of catalyst residues and/or salts from the neutralisation, separation and recovery and optional recycling of excess alcohol or excess acid, the process further comprising having at least one third reactor feed vessel, different from said first or second reactor feed vessel, comprising either a second alcohol or a second acid or anhydride, whereby said one or more esterification reactors may be fed by at least two different alcohols, at least two different acids or anhydrides, or a combination of at least two different alcohols and at least two different acids or anhydrides, and producing at least one batch of a mixed crude ester product comprising a first ester of said first alcohol and said first acid or anhydride and at least one batch of a second ester selected from the esters of said first alcohol and said second acid or anhydride, of said second alcohol and said first acid or anhydride, and of said second alcohol and said second acid or anhydride, said process comprising the method for switching production from the first ester product to the second ester product according to the present invention.

In a further embodiment of this esterification process, the at least one third reactor feed vessel shares a common flow meter and reactor valve with at least one of the first and the second feed vessel.

It is another object of the invention to provide a method wherein the appropriate selection of the first ester product and the second ester product allows for the limited amount of cross-contaminated material to be left into the products, such that the products comply with their respective product specifications as well as with the performance expectations for these products in their intended end-use. This eliminates the need to rework any cross-contaminated material or the need to downgrade this material to a lower sensitivity end-use.

It is a further object of the invention that, with an appropriate selection of the first ester product and of the second ester product, and with an appropriate value of the preselected portion in the method of the invention for switching production from the first ester product to the second and different ester product, alternatively or in combination with an appropriate selection of the timing for performing step d) in the method of the invention, mixed ester products may be obtained comprising a major portion of the first or of the second ester product, and comprising a minor portion of the other ester. We have found that the presence of the minor portion of the other ester may provide improved performance characteristics in some of the end-uses, as compared to the first or second ester in its pure form. We have also found that the level of presence of the other ester in the first or second ester can be maintained relatively constant at or around a target value, so that the composition of the mixed ester product can be tuned to the provision of the improved performance characteristics.

The invention therefore also provides for a $C_9$-$C_{11}$ alkyl benzoate composition containing at least 50% by weight of a $C_{10}$ benzoate and at least 1% and less than 10% by weight, based on the total composition, of a second ester selected from di-isononyl phthalate (DINP) and di-isononyl dicyclohexanoate (DINDCH). We have found that the presence of the phthalate or dicyclohexanoate ester, being of higher molecular weight (HMW), in the benzoate ester, which is of lower molecular weight (LMW), brings the advantage of an increased permanence as compared to the benzoate ester alone, when used in a plasticised polyvinyl chloride (PVC) composition. When the second ester is the di-cyclohexanoate, the composition may contain only non-phthalate plasticisers, and thus may have the additional advantage of containing no phthalates. Such compositions and their products may therefore be labelled phthalate-free, which for flexible PVC products such as toys, in particular for infants of 3 years old or less, medical devices, such as medical tubing, or materials made for food contact, such as film or bottle caps, may be an important property because phthalates may be an ingredient in such products that is undesirable to certain people or under certain legal provisions.

The invention further provides for several uses of the $C_9$-$C_{11}$ alkyl benzoates of the invention, as part of a polyvinyl compound, but also in several other non-vinyl applications as discussed below.

Correspondingly, and as a counterpart to the $C_9$-$C_{11}$ alkyl benzoate compositions of the current invention, when produced using the method for switching ester production according to the present invention, the invention further provides for a plasticiser composition comprising di-isononyl phthalate or di-isononyl dicyclohexanoate and further comprises at least 100 ppm by weight and less than 1% by weight of at least one $C_9$-$C_{11}$ alkyl benzoate based on the total composition.

We have found that the presence of a small amount of the LMW ester in the HMW ester may bring a surprisingly good improvement in the processing of the ester, an advantage that may be achieved without suffering an unacceptable disadvantage on the properties that are contributed by the HMW ester, such as high permanence, low volatility and/or low migration.

These and other features objects, features, and advantages will become apparent as reference is made to the following detailed description, preferred embodiments, examples, and appended claims

DETAILED DESCRIPTION

The invention is also directed to an esterification process wherein production is switched from a first ester product to a second, different, ester product. The invention is also directed to the product produced by the method of the invention, and to a system for producing a mixed-ester product.

One of the advantages of the flying grade switch procedure is its application to embodiments wherein products are produced having a wide variety of product qualities, however, it is even more advantageously suitable for a process that produces esters from only a limited number, preferably only one type, of acid or anhydride starting material, such as a process that produces primarily phthalate esters. It is still even more suitable for a process that processes only a limited number of different alcohol starting materials. If these alcohol starting materials differ in carbon number, the flying grade switch is particularly suitable if there are only small differences between the average carbon numbers of the individual alcohol qualities.

In one of the more preferred embodiments of the invention, production in a multi-product phthalate ester plant may be scheduled such that consecutive campaigns of phthalate product qualities do not differ more than about 3 carbon atoms, preferably not more than about 2 carbon atoms, and more preferably not more than about 1 carbon atoms with respect to the average carbon number of their alcohol starting materials.

The first and the second ester in the method of the invention may be selected from the group consisting of a phthalate, preferably a $C_8$-$C_{11}$ phthalate, more preferably comprising di-isononyl phthalate and/or di-isodecyl phthalate and/or di-2-ethyl hexyl terephthalate, a benzoate, preferably at least one $C_9$-$C_{11}$ alkyl benzoate, still more preferably isodecyl benzoate, and a cyclohexanoate, preferably a cyclohexanoate ester or diester of at least one $C_8$-$C_{11}$ alcohol. In particular, the first ester may be di-isononyl (di-)cyclohexanoate or di-isononyl phthalate and the second ester may be a $C_9$-$C_{11}$ alkyl benzoate, preferably including at least 50 wt % of at least one $C_{10}$ benzoate, based on the weight of the benzoate.

In the semi-continuous esterification process according to the invention, the mixed crude ester product may comprise at least one of (i) a phthalate ester and benzoate ester, (ii) a phthalate ester and a cyclohexanoate ester, and (iii) a benzoate ester and a cyclohexanoate ester, preferably wherein, if the mixed crude ester comprises a phthalate ester, this phthalate ester is selected from at least one of di-isononyl phthalate, di-isodecyl phthalate, and di-2-ethyl hexyl terephthalate, and if said mixed crude ester comprises at least one cyclohexanoate, the cyclohexanoate comprises di-isononyl cyclohexanoate, and if the mixed crude ester comprises at least one benzoate ester, the benzoate ester comprises 2-propyl-heptyl benzoate.

The present inventors have also surprisingly found that the method of the invention is particularly suitable for producing alkyl benzoate esters, preferably at least one alkyl benzoate selected from $C_9$-$C_{11}$ alkyl benzoates, such as isononyl benzoate as one of the ester products, and preferably a phthalate or a di-cyclohexanoate ester as another of the ester products, most preferably either DINP or DINDCH as the other and different ester product. If the second ester is a phthalate, the mixed ester product may be further hydrogenated to form the corresponding hexahydrophthalate or cyclohexane dicarboxylic acid diester. Suitable hydrogenation processes are disclosed in EP 1042273, US 2004/0260113 or WO 2004/046078. The benzoate ester in the mixture typically is also hydrogenated, to form the cyclohexane mono-ester. The invention therefore also provides for a composition comprising a major amount of a di-alkyl cyclohexanoate di-ester, such as di-isononyl dicyclohexanoate (DINDCH), and a minor amount of a $C_9$-$C_{11}$ alkyl cyclohexanoate mono-ester.

The invention is also directed to a product composition comprising a minor portion of a first ester (i.e., less than 50 wt %) and a major portion of a second ester (i.e., greater than 50 wt %). One of ordinary skill in the art in possession of the present disclosure will appreciate that as production is switched from one ester to a second ester, the amount of the first ester will slowly decrease as the amount of the second ester increases and that, by means of the present invention, the final average composition can be attenuated to any desired amount.

Thus, by way of example, in a preferred embodiment, the invention also provides for a $C_9$-$C_{11}$ alkyl benzoate composition containing at least 50% by weight of a $C_{10}$ benzoate and at least 1% and less than 10% by weight of at least one phthalate or cyclohexanoate ester (e.g., di-isononyl phthalate or DINP, or di-isononyl dicyclohexanoate or DINDCH) based on the total composition, more preferably 1% to 8% by weight, still more preferably 1% to 5% by weight, still more preferably 2% to 4% and typically 3% by weight, with additional embodiments including any lower weight percent listed to any higher weight percent, such as 2% to 8% by weight, and so on. In a further embodiment, as a corresponding co-product of the previously described composition, the invention further provides for a phthalate or cyclohexanoate ester product composition, e.g. a DINP or DINDCH composition comprising an analogous amount of $C_9$-$C_{11}$ alkyl benzoates, of which at least 50% by weight of the $C_9$-$C_{11}$ alkyl benzoates is at least one $C_{10}$ benzoate, i.e., 1% to less than 5% by weight, preferably 2% to 4% and typically 3% by weight of $C_9$-$C_{11}$ alkyl benzoate on the total DINP or DINDCH composition, with additional embodiments including any lower weight percent listed to any higher weight percent, such as 2% to less than 5% by weight, and so on, of the $C_9$-$C_{11}$ benzoate. By appropriate adjustment of parameters, which is within the skill of the artisan in possession of the present disclosure, such a product may be comprising, by way of further example at least 100 ppm by weight and at most 1% by weight of at least one alkyl benzoate, preferably at least one $C_9$-$C_{11}$ alkyl benzoate, e.g., isodecyl benzoate, the remainder being essentially the phthalate or cyclohexanoate ester, e.g. DINP or DINDCH.

As another preferred embodiment of the co-production scheme according to the present invention, there is a process for making a benzoate ester composition, preferably having at least one $C_9$-$C_{11}$ alkyl benzoate, containing at least 1% and less than 10% by weight of a cyclohexanoate ester, preferably di-isononyl (di-)cyclohexanoate, based on the total composition. Other esters, such as cyclohexanoate esters and diesters, may be used as the primary ester in a process and product of the invention. Thus, as an example, the invention further provides for a di-isononyl (di-)cyclohexanoate composition comprising at least 100 ppm by weight and at most 1% by weight of the described $C_9$-$C_{11}$ alkyl benzoate.

In embodiments of the invention comprising alkyl benzoate, the preferred alkyl $C_9$-$C_{11}$ benzoate is isodecyl benzoate. In still more preferred embodiment, the isodecyl benzoate is itself made by a process using as alcohol source and alcohol consisting essentially of 3-6 mol % $C_9$ alcohol or alcohol isomer, 3-9 mol % $C_{11}$ alcohol or alcohol isomer, 0.2-0.6 mol % $C_8$ alcohol or alcohol isomer, 0.2-0.6 mol % $C_{12}$ alcohol or alcohol isomer, remainder $C_{10}$ alcohol or alcohol isomer, with the product benzoate ester substantially having the corresponding mol % distribution. The term consisting essentially of as used herein means that additional impurities may be present but in amount less than 0.1 mol %. In another preferred embodiment, the alcohol source consists of a mixture of primary alcohols consisting essentially of 3-6 wt % $C_9$ alcohol isomers, 3-9 wt % $C_{11}$ alcohol isomers, the remainder being $C_{10}$ alcohol isomers. Minor amounts, such as 0.2-0.6 wt % of $C_8$ and/or $C_{12}$ alcohols may be present, as one isomer or as a mixture of isomers within each carbon number. These minor amounts are however not essential. The carbon number and isomer composition of the starting alcohol mixture may be determined by analytical methods known in the art, such as the one described in WO2006012989, or by GC, or by GC/MS, optionally after silylating the alcohols. The product benzoate ester from such an alcohol source typically has an alkyl chain composition that is identical to this of the alcohol source in terms of carbon number and isomer composition. These analytical methods are readily applicable, mutatis mutandis, to esters of these alcohols, especially mono-esters such as benzoates.

In yet still another embodiment of the invention, the production of a product comprising a phthalate ester and benzoate ester, or a phthalate ester and a cyclohexanoate ester, or a benzoate ester and a cyclohexanoate ester, is made possible by the present invention. In still a further embodiment, such a product may then be hydrogenated. In an alternative, such a product may be produced by first producing the cyclohexanoate ester, e.g., a cyclohexanoate diester of a $C_9$ alcohol, and then a benzoate ester is added post esterification employing the method of the present invention. Such a product is particularly useful in flexible PVC applications. This is an important phthalate-free product.

We have found that the $C_9$-$C_{11}$ alkyl or isodecyl benzoate containing compositions further containing at least 1% and less than 10% by weight DINP or DINDCH are particularly suitable as a viscosity depressant in PVC plastisol formulations. The composition brings the advantage that it will meet the total volatile organic compounds (TVOC's) targets as defined in the evaluation scheme for volatile organic compounds (VOC) and semivolatile organic compounds (SVOC) developed by the German Ausschuss zur gesundheitlichen Bewertung von Bauprodukten (AgBB—The Committee for health-related Evaluation of Building Products) and in line with the European Emission Test standard prEN ISO16000-9 (Determination of the emissions of volatile organic compounds from building products and furnishing—Emission test chamber method). By using this isodecyl benzoate composition as an ingredient of a product intended for indoor use, it allows the formulator to produce products that comply with the specifications that are often imposed based on these norms and tests. In particular isodecyl benzoate compositions containing at least 1% and less than 10% by weight DINP or DINDCH have been found to exhibit a lower level of SVOC's as described in the German AgBB evaluation scheme, making finished vinyl floor more suitable for indoor use.

We have also found that the benzoate compositions of the invention are particularly suitable for use as a coalescer or film-forming agent in water-based paints, caulks and/or adhesives. The HMW component will e.g. further plasticise the cured acrylic latex paint, thereby improving its room temperature flexibility, its crack resistance, and its low temperature impact strength.

The $C_9$-$C_{11}$ alkyl or isodecyl benzoate compositions according to the invention may be used in polyvinyl chloride (PVC) compounds at relatively low concentrations, such as 2-20 phr (per hundred resin, or parts per hundred parts of PVC), in order to enhance processability. The improve PVC fusion, lower plastisol and melt viscosities and improve the foam quality of foamed PVC compounds. This is particularly suitable when cyclohexanoate diesters are used as the plasticisers in the compound, as these tend to have a higher fusion temperature than phthalate esters with similar alcohols or alcohol mixtures of similar compositions. For example, DINDCH has a higher fusion temperature than DINP, and a PVC compound based on DINDCH, but with the isodecyl benzoate composition of the invention added to an amount of 5-40% wt of the plasticiser system, will show a much enhanced processability as compared to the same compound with only DINDCH as the plasticiser. Preferably in this DINDCH-based compound, the isodecyl benzoate composition contains DINDCH as the second ester, so that the compound can be labeled as "phthalate free", a label that may be important in particular sensitive applications such as toys, medical, food contact materials, or indoor applications such as flooring and wallcovering. Specific types of products which can benefit from addition of 2-20 phr of the $C_9$-$C_{11}$ alkyl or isodecyl benzoate composition according to the invention are PVC-wood composites, plastisol coated meshes, screens and webs, plastisol coated monofilament, carpet tiles, rotomolded and injection molded toys and plastisol foams.

In sensitive applications like the production of toys intended to be put in the mouth, or some of the medical articles like medical investigation gloves, regulatory agencies are reducing or limiting the tolerated amount of phthalate esters that can be used as primary plasticisers. The replacement non-phthalate plasticisers, such as di-benzoate esters, citrates and the already mentioned di-cyclohexanoates (or hydrogenated phthalates) often result in PVC compositions having either a higher gelation and/or fusion temperature, in plastisols having an increased viscosity and/or a greater tendency towards dilatancy, or in compounds having an increased melt viscosity. "Dilatancy" is a flow property of liquids. A liquid shows dilatant flow if its viscosity increases as the rate at which it is sheared increases. This type of flow is generally undesirable in plastisols. Viscosity of a dilatant plastisol can increase to the point where the plastisol tears or rips apart during a roll coating or knife coating process, for example. Shear thinning flow, in which viscosity decreases with increasing shear or Newtonian flow in which viscosity does not change with increasing shear are generally more desirable in industrial processes. In plastisols, dilatant flow may result from using a plasticizer which is very strongly attracted to the polymer. On the other hand, plasticizers with much less attraction to the PVC polymer can give higher plastisol gelation and fusion temperatures. This may lead to articles with poorer mechanical properties, often introduced because of uneven thicknesses such as for example non-spherical playballs. Compounds and the articles derived thereof can benefit from the addition of 2-40 phr of $C_9$-$C_{11}$ alkyl or isodecyl benzoate according to the invention, because of the improved fusion, the lower plastisol and melt rheologies. They also benefit from a lower compound density brought by the lower density of the isodecyl benzoate, as compared to the other non-phthalate compounds, in particular the diethylene glycol dibenzoate or the acetyl tri-n-butyl citrate, which have a higher density at the same temperature. The $C_9$-$C_{11}$ alkyl or isodecyl benzoate therefore also provides a volume cost advantage to the formulator of the compound and/or of the article. The compound or article will have a lower weight for the same volume, which brings benefit in handling, storage and transport. The lower odour and/or colour of the $C_9$-$C_{11}$ alkyl or isodecyl benzoate will also improve the look and feel of the finished article and increase the comfort during use.

The alkyl benzoate compositions according to the invention may also be used in polyurethane foams, in particular in low density PU foams that may be used as structural materials, as acoustical barriers, in household products, bedding and upholstered products and in many other end-uses. In each of these cases, the PU foam, upon creation, comprises a gas-in-liquid foam. In low density foams, gas cells are separated by thin walls or lamellae made up of the liquid PU and/or PU prepolymers which soon polymerise and solidify. The gas-in-liquid foams are however thermodynamically unstable and typically must be stabilised for the finished product to be useful. Greater internal pressures in the smaller cells and surface tension gradients in the draining lamellae may encourage cells to rupture and coalesce at this stage. Typically surfactants, and often silicones, are used as stabilisers for the gas-in-liquid PUR foams. Addition of small amounts of the $C_9$-$C_{11}$ alkyl or isodecyl benzoate compositions according to the invention further reduces the viscosity of the material forming the lamellar walls, which may lead to thinner but more uniform walls, which still have sufficient surface tension to prevent film rupture and which are therefore less prone to break. Use of the $C_9$-$C_{11}$ alkyl or isodecyl benzoate compositions imparts the added benefit of some plasticity to the fully reacted PUR foam.

The $C_9$-$C_{11}$ alkyl or isodecyl benzoate compositions according to the invention may also be used as effective fluids for coil coating applications. Coil coating are applied to a continuous steel or aluminum coil, usually by a dip method, and subsequently cured in seconds in a hot oven and recoiled for transport to the coil customer. The coil may then be cut and formed into the desired product, such as e.g. a rain gutter. High boiling, strong solvents such as Aromatic 200 of ExxonMobil Chemical Company are commonly used in this application as the diluents and/or viscosity depressants for these coil coatings. Other high boiling solvents used include high molecular weight esters. A high flash point, a low volatility and a high stability are keys to a good solvent as the substrate temperatures are typically 210-250° C. Production lines run fast, readily in the range of 200-220 meter/minute. Typically, first a primer is applied in a thickness of 5-35 micrometer, and a finishing layer is applied in a thickness of 15-200 micrometer. The $C_9$-$C_{11}$ alkyl or isodecyl benzoate compositions have a strong solvency and a low odour. Their viscosity range make them attractive candidates as a solvent in coil coatings. They may still bring a benefit in terms of volatile organic compound emission over the high boiling solvents that are typically used today, as well as an odour benefit.

The $C_9$-$C_{11}$ alkyl or isodecyl benzoate compositions according to the invention may also be used as an effective blanket wash for litho presses. A finished ink typically contains varnish, pigment flush and additional solvents and additives. In litho printing, it is the blanket which transfers ink to the substrate. The blanket consists of a backing fabric which is woven and laminated in thin layers and then coated with a synthetic rubber or similar compound. Modern presses have automatic blanket washing which use cleaning fluids called blanket washes to remove the ink from the blanket. Paraffin hydrocarbon solvents are commonly used to make a blanket wash. Examples are Exx-Print™ 283 D and Exx-Print™ 588 D fluids. Co-solvents, such as TXIB (Texanol Isobutyrate) or isotridecyl alcohol (such as Exxal™ 13) are often added to the blanket wash to improve the cleaning power. When necessary, these oxygenated solvents are used neat as a blanket wash, if the ink dictates their use. The $C_9$-$C_{11}$ alkyl or isodecyl benzoate compositions according to the invention may be used as co-solvents in blanket washes. They may also be used as neat blanket washes. These esters provide the necessary solvency strength and have the appropriate evaporation and viscosity profiles similar to TXIB. The lower vapor pressure and volatility may further bring benefits in lower emissions of volatile organic compounds (VOC), in particular over the traditional hydrocarbon fluids used in this application.

The $C_9$-$C_{11}$ alkyl or isodecyl benzoate compositions according to the present invention are also useful as co-solvents in printing ink formulations. Printing inks generally contain pigments for coloration, resins to form the ink film, additives to impart special properties and solvents for viscosity control and to carry the ingredients to the substrate. Resins are solids or semi-solid organic substances which bind the pigments to the printed surface. An ink varnish or vehicle is made by dissolving resin and additives in solvent. A pigment flush is pre-dispersed pigment in resin, solvent, and additives. A finished ink typically contains varnish, pigment flush and additional solvent and additives. Paraffin hydrocarbon solvents are commonly used to make a varnish for a past ink. Examples are Exx-Print™ 283 D and Exx-Print™ 588 D fluids. Co-solvents such as the above cited TXIB and Exxal™ 13 are often added to the varnish to improve the resin-solvent compatibility, to reduce tack and/or to adjust viscosity. Co-solvents are also added to the pigment flush to provide improved solvency and/or to reduce viscosity. Co-solvents may also be added to the finished ink to adjust viscosity and/or dissolve additives. The $C_9$-$C_{11}$ alkyl or isodecyl benzoate compositions, by the structure and molecular weight of the components, are useful as co-solvents in printing ink formulations, providing the necessary solvency strength and appropriate evaporation profiles to displace currently used products such as TXIB.

The $C_9$-$C_{11}$ alkyl or isodecyl benzoate compositions according to the present invention are also useful as solvents, preferably as prime solvents, for carbonless copy paper (CCP). CCP is made using a microencapsulation process. A conventional CCP set consists of three sheets of paper, one original and two copies. The top sheet, i.e. the original, has a plain front and is coated with microcapsules on the back. The middle sheet, i.e. the first copy, is coated with a developer on the front and with microcapsules on the back. The bottom sheet, here thus the second copy, is coated with a developer on the front and is plain on the back. Alternatively there may be more than three sheets, with each of the "middle sheets" coated as the first copy. The microcapsules contain colorformers, so-called dyes, that change color when they come in contact with the developer. Solvents are used as carriers for the colorformers in the dyes. Prime solvents are used to dissolve the colorformers and diluent solvents are used to reduce solution viscosity. When the microcapsules are broken, such as by a pen or a printer head impressing on the front of the original, the encapsulated colorformer solution comes in contact with the developer, and the color change forms an image on the fronts of the first and subsequent copy pages. The $C_9$-$C_{11}$ alkyl or isodecyl benzoate compositions are suitable prime solvents in CCP. They have the high solvency power needed to dissolve the colorformers sufficiently, and are compatible with the diluent solvents used, such as marketed by ExxonMobil Chemical. The $C_9$-$C_{11}$ alkyl or isodecyl benzoate compositions offer solvency characteristics similar to or better than competitive products currently used, such as di-isopropylnaphthalene, isopropylbiphenyl, hydrogenated terphenyl and chloroparaffins. They also meet the general requirements for prime and diluent solvents, such as high purity, low odour, high light stability and they have the appropriate molecular weight to dry by absorption. The $C_9$-$C_{11}$ alkyl or isodecyl benzoate compositions offer compatibility with a wide variety of microcapsule ingredients, such as polyamide, polyurethane, polyvinyl alcohol or acrylic resins, as well as with the developer layer, which typically contains a clay or phenolic resins. The presence of the second ester of even higher molecular weight than the benzoate in the composition, such as the phthalate or the cyclohexanoate diester, in particular the DINP or DINDCH, imparts a higher permanence of the formed image.

The $C_9$-$C_{11}$ alkyl or isodecyl benzoate compositions according to the present invention are also useful as primary solvents or cosolvents in liquid agricultural chemical formulations, particularly in low volume, ultra-low volume or emulsifiable agricultural chemical concentrate formulations. Liquid formulations are the preferred way to handle agricultural chemical products because of their lower cost of manufacture and the ease of handling. The $C_9$-$C_{11}$ alkyl or isodecyl benzoate compositions bring physical properties that are complimentary to the solvents currently used in this end-use. Their solvency is strong and unique, believed to be derived from the polarity and hydrogen bonding of the esters, combined with the dispersive force of the aromatic ring. They therefore display an affinity for many chemical types of active ingredients. The volatility of the formulation controls the residence time an active ingredient remains on the surface of a plant or an insect. The $C_9$-$C_{11}$ alkyl or isodecyl benzoates offer a suitable evaporation rate and the correct flash point for such formulations. In addition, they meet the low vapour pressure regulatory requirements, such that they are non-reportable as VOC and exempt from VOC reporting considerations. Their low pour point offers benefits for use of the formulations in cold climates. They also offer a low solubility in water, such that they impart enhanced storage stability to emulsifiable concentrates of which the active ingredients may be unstable or insoluble in water. The benzoate compositions also have a low level of phytotoxicity, such that their use in the formulation will pose minimal phytotoxic risk. The high solvency, acceptable water miscibility and low temperature properties make these benzoate compositions excellent carriers in emulsifiable concentrates.

The following examples are meant to illustrate and not limit the present invention. Numerous modifications and variations are possible and it is to be understood that within the scope of the appended claims, the invention may be practiced otherwise than as specifically described herein.

In this example a grade switch is described from an old grade product to a new grade product. It is assumed that there is a higher level of tolerance of contamination of the old grade product into the new grade product, as compared to the opposite contamination. This is for instance the case when the old grade is a HMW ester, such as a phthalate or cyclohexanoate di-ester, in particular DINP or DINDCH, and the new grade is a LMW ester, such as a C9 to C11 alkyl benzoate ester, such as isodecyl benzoate. The grade switch procedure is described here for a change from DINP to isodecyl benzoate.

The flying grade-switch is executed by maximizing the feed rate to the finishing unit, while having at the same time a minimum liquid hold up. As a preparation for a flying grade-switch, exemplified here in a batch reactor unit combined with a continuous finishing unit, all vessel levels are gradually reduced to the minimum level required to keep the esterification unit pumps and mixers running. This also allows for a continued operation of the solids addition systems. Furthermore, all precoat filters are being switched just before or just after the completion of the first batch of the new grade. The precoat vessel, where the filter precoat material is mixed with liquid before transfer to the filter system, is being emptied into the primary filtration feed vessel prior to the grade switch.

The alcohol feed line and the alcohol feed vessel are being emptied into the last reactor batch of the old grade. In tankage, the feed alcohol and recycle alcohol vessels are then switched over from iso-nonyl alcohol to the new grade isodecyl alcohol, and the reactor feed tank is filled with the new alcohol grade. The acid feed system is switched from the phthalic anhydride vessel to the benzoic acid vessel. At the reactor the phthalic anhydride (PAN) valves are closed followed by opening the benzoic acid valves. The feed system comprises of a pump, flow measurement (e.g. a coriolis system or turbine meter) and isolation block valves. The new grade recipe is loaded into the reactor process control system. The reactor section is now ready for the production of the first batch of the new grade.

After dumping the last batch of crude ester of the old grade, the feed tank of the continuous finishing unit is gradually emptied to reach about 2% tank level, which is sufficient to keep the finishing unit feed pump running, just before dumping the first batch of the new grade into that tank. After dumping the first batch of the new grade into the finishing feed tank, the hydrolysis water ratios are typically adjusted to the requirements of the new grade.

After feeding 35% of the total volume of the new crude ester required for flushing out the old ester from the continuous finishing section, also called the required flushing volume, the level control valve of the water flash tank is closed and the filter aid addition to the mixing vessel of the primary filtration step is stopped. This mixing vessel is nearly emptied followed by opening the level control valve of the flash vessel, while maintaining a low level of 4% in the mixing vessel.

At this time, the adsorbent and/or filter aid solids addition to the feed vessel of the secondary filtration unit, which is typically located downstream of the excess alcohol stripper tower, is preferably also stopped, and this preferably when the vessel content has first been reduced to its minimum level of 40% to keep the mixer of this vessel running.

After feeding 45% of the total required flushing volume, the liquid circulation flows over the secondary filtration unit and its dosing system are also stopped, while the stripper feed preheater temperature is adjusted to the new conditions.

After feeding 65% of the total required flushing volume, the mixer in the feed vessel of the secondary filtration unit is stopped. The feed from the product drying tower to this vessel is stopped to allow for nearly emptying the feed vessel to the secondary filtration unit. After reaching a level of 8 vol % the feed to the vessel is restored and kept at his level. The alcohol product from the stripper tower is now switched from the old alcohol grade recycle alcohol vessel to the new alcohol grade recycle alcohol vessel and used as recycle alcohol feed for the esterification reactors.

When reaching 85% of the required flushing volume, the operator starts checking the density of the plasticizer rundown product. This density can be measured by taking a sample and using a conventional density measurement technique, typically a manual technique. Alternative it can be done by using an on-line continuous density measurement, which gives an even faster response and does not involve manpower.

As soon as the density measurement shows the target plasticizer density for the new grade, the rundown of the unit is switched from the old grade to the new grade vessel. The circulation flows over the primary and secondary filtration unit and their dosing systems are restarted. The filtration vessel levels are being re-established followed by restarting the mixers and the adsorbent and/or filter aid dosing systems. All other vessel levels are now being returned to their target values, preferably in a gradual fashion.

For the switch back from the new grade to the old grade the sequence of steps and check points are the same, except that only after reaching 100% of the required flushing volume the operator starts checking the density of the plasticizer product, and upon measuring the new target density, continues the grade switch.

In a preferred embodiment, the pumping rate is high, which allows for an almost plug-flow type behaviour thereby minimizing the cross-contamination.

The present inventors have found that the flying grade switch procedure may be applied to a process that produces a wide variety of product qualities. The present inventors have also found that it is particularly suitable for a process that produces esters from only a limited number, preferably only one type, of acid or anhydride starting material, such as a process that produces primarily phthalate esters. It is even more suitable for a process that processes only a limited number of different alcohol starting materials. If these alcohol starting materials differ in carbon number, the flying grade switch is particularly suitable if there are only small differences between the average carbon numbers of the individual alcohol qualities. It is preferred to schedule production in a multi-product phthalate ester plant such that consecutive campaigns of phthalate product qualities do not differ more than about 3 carbon atoms, preferably not more than about 2 carbon atoms, and more preferably not more than about 1 carbon atom with respect to the average carbon number of their alcohol starting materials. Such production sequences allow to apply the advantageous flying grade switch procedure while minimizing the degree of product cross-contamination, that is inevitable in such procedure, and any possible effect thereof on product performance. It is also preferred to run the campaigns of a single product quality as long as possible, i.e. with as many as possible consecutive batches, as allowed by feed availability, product storage capacity, and product demand. This further reduces the amount of product cross-contamination between two consecutive product campaigns.

The $C_9$-$C_{11}$ alkyl or isodecyl benzoate composition according to the invention may be produced from an isodecyl alcohol comprising 2-propyl-heptanol as the major component. The isodecyl benzoate may therefore comprise at least 50% of 2-propyl-heptyl benzoate.

In a preferred embodiment, the process of the invention provides for common feed flow meters and reactor valves for the raw materials, thereby minimizing costs.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention.

Having now fully described this invention, it will be appreciated by those skilled in the art that the invention can be performed within a wide range of parameters within what is claimed, without departing from the spirit and scope of the invention.

The invention claimed is:

1. A method for switching production from a first ester product to a second and different ester product, in an esterification process that comprises a feed vessel for feeding a continuous finishing section which comprises at least one filtration step using solids addition for precoating a precoat filter, comprising the steps of before introducing the second ester product into the feed vessel,
  a) reducing the level of said feed vessel,
  b) optionally switching the precoat filter in service to a filter with a fresh precoat layer, c) reducing the level of precoat containing liquid in the filter precoat vessel, introducing the second ester product into the feed vessel of the continuous finishing section, and after feeding to the feed vessel a preselected portion of the volume of the second ester, required for flushing out the first ester from the continuous finishing section, d) redirecting the product rundown of the finishing section from the vessel receiving the first product ester to a different vessel for receiving the second product ester, e) optionally re-establishing increased liquid levels in the filter precoat vessel and in the feed vessel to the continuous finishing section.

2. The method according to claim 1 further comprising switching production from the second ester product to a second campaign of the first ester product, using steps a), b), c), d), and e), whereby the redirecting in step d) is performed after feeding at least 90% and preferably 100% of the volume of the first ester, required for flushing out the second ester from the continuous finishing section.

3. An esterification process for producing a first ester product and subsequently producing a second ester product comprising the method for switching production from the first ester product to the second ester product according to claim 1.

4. The esterification process according to claim 3 operated in semi-continuous mode, wherein one or more esterification reactors are fed from at least a first reactor feed vessel comprising a first alcohol and at least a second reactor feed vessel comprising a first acid or anhydride, and wherein the crude ester product from said one or more esterification reactors is collected in batches and processed continuously through a finishing section for at least one of catalyst removal, neutralisation of leftover traces of acid, separation of catalyst residues and/or salts from the neutralisation, separation and recovery and optional recycling of excess alcohol or excess acid, the process further comprising having at least one third reactor feed vessel, different from said first or second reactor feed vessel, comprising either a second alcohol or a second acid or anhydride, whereby said one or more esterification reactors may be fed by at least two different alcohols, at least two different acids or anhydrides, or a combination of at least two different alcohols and at least two different acids or anhydrides, and producing at least one batch of a mixed crude ester product comprising a first ester of said first alcohol and said first acid or anhydride and at least one batch of a second ester selected from the esters of said first alcohol and said second acid or anhydride, of said second alcohol and said first acid or anhydride, and of said second alcohol and said second acid or anhydride.

5. The process of claim 3, wherein at least one of said first ester product and said second ester product comprises at least one phthalate, whereby a mixed ester product is produced comprising said at least one phthalate, and the process is further characterized by a step of hydrogenating said mixed ester product comprising said at least one phthalate, preferably after processing through the finishing section.

* * * * *